(12) United States Patent
Woo et al.

(10) Patent No.: US 7,759,368 B2
(45) Date of Patent: Jul. 20, 2010

(54) SUSTAINED RELEASE COMPOSITION FOR ORAL ADMINISTRATION OF NIACIN

(75) Inventors: Jong Soo Woo, Suwon-si (KR); Young Hun Kim, Suwon-si (KR)

(73) Assignee: Hanmi Pharm. Co., Ltd, Kyungki-do (KR)

( * ) Notice: Subject to any disclaimer, the term of this patent is extended or adjusted under 35 U.S.C. 154(b) by 762 days.

(21) Appl. No.: 11/569,269

(22) PCT Filed: May 27, 2005

(86) PCT No.: PCT/KR2005/001566

§ 371 (c)(1),
(2), (4) Date: Nov. 17, 2006

(87) PCT Pub. No.: WO2005/115387

PCT Pub. Date: Dec. 8, 2005

(65) Prior Publication Data

US 2009/0042952 A1   Feb. 12, 2009

(30) Foreign Application Priority Data

May 28, 2004   (KR) .................... 10-2004-0038026

(51) Int. Cl.
*A61K 31/44* (2006.01)
*A61F 2/00* (2006.01)
*A61K 9/22* (2006.01)

(52) U.S. Cl. .................. 514/356; 424/426; 424/468

(58) Field of Classification Search ............... None
See application file for complete search history.

(56) References Cited

U.S. PATENT DOCUMENTS

| 5,126,145 | A | | 6/1992 | Evenstad et al. |
| 5,654,005 | A | * | 8/1997 | Chen et al. ............. 424/480 |
| 6,129,930 | A | * | 10/2000 | Bova ....................... 424/468 |
| 6,406,715 | B1 | | 6/2002 | Cefali |
| 6,500,459 | B1 | | 12/2002 | Chhabra et al. |
| 2003/0021841 | A1 | | 1/2003 | Matharu et al. |

FOREIGN PATENT DOCUMENTS

EP   WO97/18814   *   5/1997

OTHER PUBLICATIONS

Atlaf et al, 1998. Guar gum-based sustained release diltiazem. Pharmaceutical Research, vol. 15(8):1196-1201.*
Shao et al, 2001. Effects of formulation variables and post-compression curing on drug release from a new sustained-release matrix material: Polyvinylacetate-Povidone. Pharmaceutical Development and Technology, vol. 6(2):247-254.*

* cited by examiner

*Primary Examiner*—Jean C. Witz
*Assistant Examiner*—Raymond P Yeager
(74) *Attorney, Agent, or Firm*—Sughrue Mion, PLLC

(57) ABSTRACT

A sustained release composition for oral administration of niacin, comprising niacin; a carrier for sustained release composed of a hydrophilic polymer and a hydrophobic polymer; and a pharmaceutically acceptable additive, the hydrophilic polymer being a polyethylene oxide and a natural gum, is capable of maintaining a constant release rate of niacin.

5 Claims, 4 Drawing Sheets

SUSTAINED RELEASE COMPOSITION FOR ORAL ADMINISTRATION OF NIACIN

FIELD OF THE INVENTION

The present invention relates to a sustained release composition for oral administration of niacin.

BACKGROUND OF THE INVENTION

Niacin acts to reduce the low density lipoprotein cholesterol and triglyceride levels in the blood, and its oral medication is used for treating hypercholesterolemia, hypertriglyceridemia and diseases induced thereby.

Niacin is commercially available in the form of NIASPAN® (Kos Pharmaceuticals, Inc.) tablet which contains niacin in a 500 mg, 750 mg or 1000 mg unit, and its daily dosage is determined individually on the basis of both effectiveness and tolerance, while not exceeding the maximum recommended dose of 2,000 mg per day. Niacin causes side effects such as nausea, abdominal distension, diarrhea and flushing, which can be avoided by reducing the minimum and/or maintenance dose, or by administrating a sustained release composition.

Existing sustained release compositions of niacin are based on using a hydrophilic polymer of hydroxypropyl methylcellulose as a carrier for sustained release of niacin. For example, U.S. Pat. No. 6,406,715 discloses a timed-release niacin formulation comprising niacin and hydroxypropyl methylcellulose; and U.S. Pat. No. 5,126,145 discloses a sustained release niacin formulation comprising two different types of hydroxypropyl methylcellulose and a hydrophobic component. However, such existing sustained release compositions have the problem of complicated production procedures and high production costs.

Therefore, there has been a need to develop a sustained release composition of niacin which can be produced by an economic process.

SUMMARY OF THE INVENTION

Accordingly, it is an object of the present invention to provide a sustained release composition of niacin, which can maintain uniform release of niacin for a long period of time and can be easily prepared.

In accordance with one aspect of the present invention, there is provided a sustained release composition for oral administration of niacin, comprising niacin as an active ingredient; a carrier for sustained release composed of a hydrophilic polymer and a hydrophobic polymer; and a pharmaceutically acceptable additive, wherein the hydrophilic polymer is a mixture of a polyethylene oxide and a natural gum.

BRIEF DESCRIPTION OF DRAWINGS

The above and other objects and features of the present invention will become apparent from the following description of the invention taken in conjunction with the following accompanying drawings, which respectively show.

DETAILED DESCRIPTION OF THE INVENTION

Figure 1:
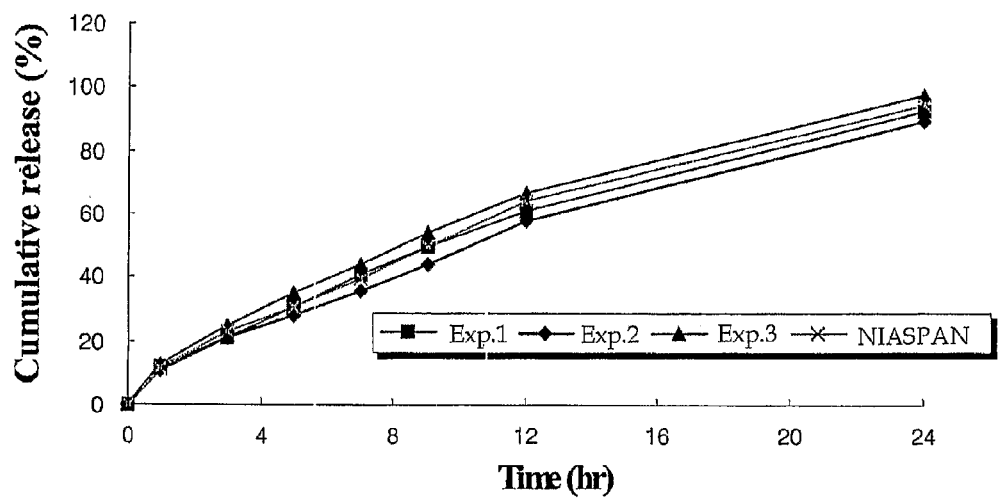
FIG. 1: in vitro release profiles of sustained release tablets prepared in Examples 1 to 3 of the present invention and a comparative formulation (NIASPAN®)
Figure 2:
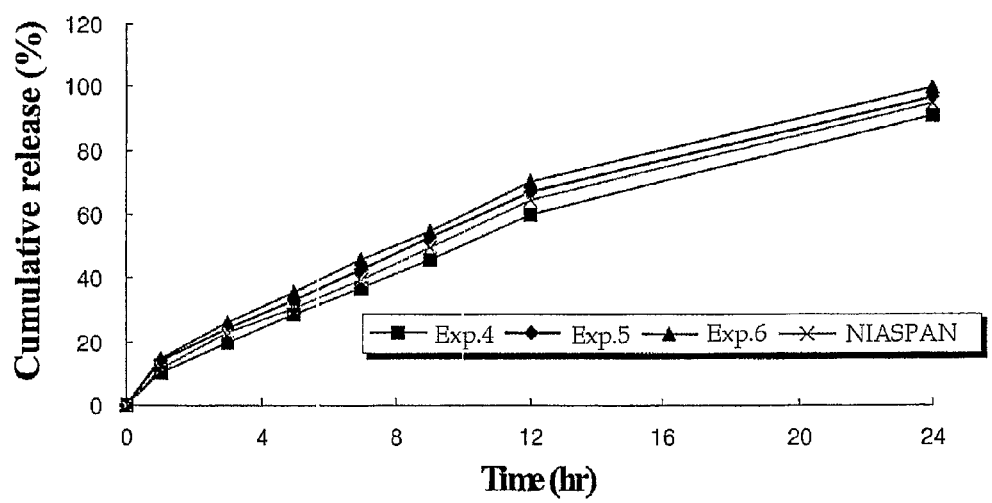
FIG. 2: in vitro release profiles of the sustained release tablets prepared in Examples 4 to 6 of the present invention and a comparative formulation (NIASPAN®)
Figure 3:
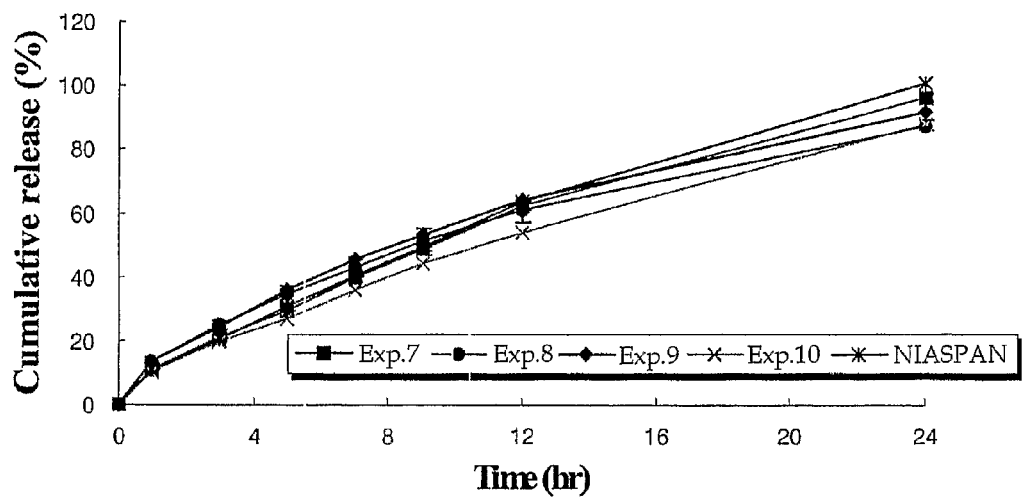
FIG. 3: in vitro release profiles of the sustained release tablets prepared in Examples 7 to 10 of the present invention and a comparative formulation (NIASPAN®)
Figure 4:
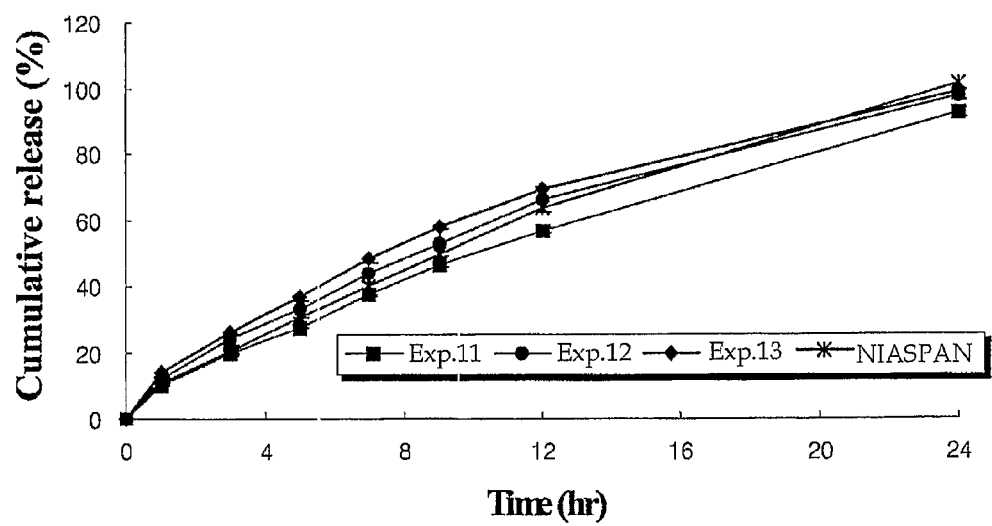
FIG. 4: in vitro release profiles of the sustained release tablets prepared in Examples 11 to 13 of the present invention and a comparative formulation (NIASPAN®)

The inventive sustained release composition of niacin can maintain a constant release rate of highly water-soluble niacin by using a carrier for sustained release composed of a hydrophilic polymer, which is a mixture of a polyethylene oxide and a natural gum, and a hydrophobic polymer.

Each ingredient of the inventive composition is described in detail as follows:

(1) Pharmaceutically Active Ingredient

The active ingredient of the sustained release composition of the present invention is niacin used for treating hyperlipidemia.

(2) Carrier for Sustained Release

The carrier for sustained release of the present invention composes of a hydrophilic polymer, which is a mixture of a polyethylene oxide and a natural gum, and a hydrophobic polymer.

The polyethylene oxide may be selected from the ones having an average molecular weight ranging from 100,000 to 7,000,000, or a mixture of two or more polyethylene oxides with different molecular weights may be also used.

The natural gum used in the present invention may be xanthan gum, locust bean gum, guar gum, or a mixture thereof.

The hydrophobic polymer used in the present invention may be polyvinylacetate, a polyvinylacetate/polyvinylpyrrolidone mixture, wax or a mixture thereof. Among these, a polyvinylacetate/polyvinylpyrrolidone mixture which is commercially available by Kollidon® SR (BASF, Germany) is particularly preferred.

In accordance with the present invention, the weight ratio of the active ingredient:carrier for sustained release preferable ranges from 1:0.01 to 1:1, preferably from 1:0.1 to 1:0.5. For the carrier, the weight ratio of hydrophilic polymer:hydrophobic polymer preferable ranges from 1:0.1 to 1:2.0. For the hydrophilic polymer, the polyethylene oxide and the natural gum are preferably mixed in a weight ration ranging from 1:0.01 to 1:5.0, preferably from 1:0.1 to 1:4.0.

(3) Pharmaceutically Acceptable Additive

The pharmaceutical composition of the present invention may be formulated for oral administration. The formulation for oral administration may take various forms such as tablet, pill, powder, sachet, soft and hard capsule, solution, suspension, emulsion, syrup, granule, chewable tab, jelly and the like, which may contain conventional additives such as a diluent (e.g., lactose, dextrose, sucrose, mannitol, sorbitol, cellulose and/or glycine), a lubricant (e.g., silica, talc, stearic acid or its zinc, magnesium or calcium salt, and/or polyethylene glycol), a binder (e.g., magnesium aluminum silicate, starch paste, gelatin, tragacanth, methyl cellulose, sodium carboxylmethyl cellulose and/or polyvinylpyrrolidone, hydroxypropyl cellulose and kofobidon (Kollidon® VA64, BASF, Germany), and optionally a disintegrant (e.g., starch, agar, alginic acid or its sodium salt), an effervescent mixture, an absorbent, a colorant, a flavor and a sweetener.

Preferably, a tablet may be produced in a dual system consisting of a granule-forming part and a mixture part wherein each part may contain a part of the carrier for sustained release. The granule-forming part may further comprise a binder such as polyvinylpyrrolidone so as to aid the stability of the drug flow.

In accordance with the present invention, the weight ratio of the active ingredient:pharmaceutically acceptable additives may range from 1:0.001 to 0.1, and preferably, from 1:0.005 to 0.05.

The composition may be steriled, and may additionally include preservatives, stabilizers, wetting agents, emulsifying agents, osmotic pressure-adjusting agents, buffering agents and the like.

The inventive pharmaceutical composition may be administered daily. A typical daily dose of the active ingredient ranges from about 1 to 60 mg/kg, preferably 5 to 40 mg/kg, and can be administered in a single dose or in divided doses. However, it should be understood that the amount of the active ingredient actually administered should be determined in light of various relevant factors including the condition to be treated, the chosen route of administration, the age and weight of the individual patient, and the severity of the patient's symptoms; and, therefore, the dosage suggested above should not be construed to limit the scope of the invention in any way.

The following Examples are intended to further illustrate the present invention without limiting its scope.

EXAMPLES

Preparation of Niacin Sustained release Tablet

Example 1

500 g of niacin (Danil fine chemicals corporation) and 38 g of polyethylene oxide (Polyox® WSR Agglutinant, Molecular weight 5,000,000, Union Carbide) were each filtered through No. 30 mesh and mixed together. The mixture was placed in a high-speed mixer (SPG-2, Fujipaudal), and a binder solution made up of 14 g of polyvinyl pyrrolidone (Kollidon® K-90, BASF) dissolved in distilled water/isopropyl alcohol mixture (1:1 v/v) was added to the mixer, followed by mixing at a rate of 100~1,000 rpm for 3 min to obtain granules. The granules were dried and filtered through No. 30 mesh. Thereafter, 75 g of a polyvinyl acetate/polyvinyl pyrrolidone mixture (Kollidon® SR, BASF), 37 g of xanthan gum (Cpkelco), 22 g of locust bean gum (Sigma, USA) and 7 g of silicon dioxide were added to the granules and mixed for 30 min. Finally, 7 g of magnesium stearate powder was added to the mixture, mixed for 3 min, and compressed to obtain a tablet having the composition of Table 1.

Examples 2 to 13

Tablets having the compositions listed in Table 1 were prepared by repeating the procedure of Example 1.

TABLE 1

| | Granule forming part | | | Mixture part | | | | |
|---|---|---|---|---|---|---|---|---|
| | | | | Polyvinyl acetate/ | | | | |
| | Niacin | Polyethylene oxide | | Polyvinyl pyrrolidone | Polyvinyl pyrrolidone mixture | Xanthan gum | Locust bean gum | Silicon dioxide | Magnesium stearate |
| Ex. | (wt %) | (wt %) | M.W | (wt %) | (wt %) | (wt %) | (wt %) | (wt %) | (wt %) |
| 1 | 71.4 | 5.4 | 5,000,000 | 2.0 | 10.7 | 5.3 | 3.1 | 1.0 | 1.0 |
| 2 | 71.4 | 5.4 | 5,000,000 | 2.0 | 9.3 | 6.0 | 3.9 | 1.0 | 1.0 |
| 3 | 71.4 | 5.4 | 5,000,000 | 2.0 | 12.1 | 4.4 | 2.6 | 1.0 | 1.0 |
| 4 | 71.4 | 2.9 | 5,000,000 | 2.0 | 10.7 | 6.7 | 4.3 | 1.0 | 1.0 |
| 5 | 71.4 | 5.4 | 900,000 | 2.0 | 10.7 | 5.3 | 3.1 | 1.0 | 1.0 |
| 6 | 71.4 | 5.4 | 100,000 | 2.0 | 10.7 | 5.3 | 3.1 | 1.0 | 1.0 |
| 7 | 85.5 | 2.9 | 5,000,000 | 2.1 | 6.0 | 1.1 | 0.8 | 0.9 | 0.9 |
| 8 | 83.3 | 2.8 | 5,000,000 | 2.0 | 6.9 | 1.8 | 1.2 | 1.0 | 1.0 |
| 9 | 83.3 | 2.8 | 5,000,000 | 2.0 | 7.9 | 1.2 | 0.8 | 1.0 | 1.0 |
| 10 | 85.2 | 2.9 | 5,000,000 | 2.0 | 6.0 | 1.3 | 0.9 | 0.9 | 0.9 |
| 11 | 84.3 | 4.2 | 5,000,000 | 2.0 | 5.9 | 1.1 | 0.7 | 0.8 | 0.8 |
| 12 | 85.5 | 2.9 | 900,000 | 2.1 | 6.0 | 1.1 | 0.8 | 0.9 | 0.9 |
| 13 | 85.5 | 2.9 | 100,000 | 2.1 | 6.0 | 1.1 | 0.8 | 0.9 | 0.9 |

Comparative Examples 1 to 3

The tablet having the composition listed in Table 2 was prepared by repeating the procedure of Example 1.

TABLE 2

| | Granule forming part | | | Mixture part | | | | |
| --- | --- | --- | --- | --- | --- | --- | --- | --- |
| | | Polyethylene oxide | | Polyvinyl acetate/ | | | | |
| Com. | Niacin | | | Polyvinyl pyrrolidone | Polyvinyl pyrrolidone mixture | Xanthan gum | Locust bean gum | Silicon dioxide | Magnesium stearate |
| Ex. | (wt %) | (wt %) | M.W | (wt %) | (wt %) | (wt %) | (wt %) | (wt %) | (wt %) |
| 1 | 88.0 | — | — | 2.1 | 6.2 | 1.2 | 0.8 | 0.9 | 0.9 |
| 2 | 90.9 | 3.1 | 5,000,000 | 2.2 | — | 1.2 | 0.8 | 0.9 | 0.9 |
| 3 | 87.1 | 3.0 | 5,000,000 | 2.0 | 6.1 | — | — | 0.9 | 0.9 |

Test Example 1

In Vitro Release-Test

The tablets prepared in Examples 1 to 13 and NIASPAN® sustained release tablet (Kos Pharmaceuticals, Inc.) as a comparative formulation were subjected to in vitro release-test in accordance with the release-test method described in Korea pharmacopoeia (the paddle method) so as to compare the effectiveness of polyethylene oxide, natural gum and polyvinyl acetate/polyvinyl pyrrolidone mixture as a carrier for sustained release in terms of the release rate. The release pattern of niacin from each of the tablets was measured under the following conditions.

Release-test system: Erweka DT 80
Release solution: The disintegrating-test 3nd method described in Korea pharmacopoeia (water)
Temperature of release solution: 37±0.5° C.
Amount of release solution: 900 ml
Rotation rate: 50 rpm
Sample collection time: Aliquots of the release solution were collected at 1, 3, 5, 7, 9, 12 and 24 hr, filtered through a 0.45 µm membrane, and used as test samples. After sampling the release solution, the release-test system was refilled with an equal amount of fresh release solution.
Analyzing method: Absorbances of the samples and a standard solution were measured at 260 nm employing distilled water as a reference to calculate corresponding release ratios.
Calculation of released amount: Cumulative release amount As can be seen from FIGS. 1 to 4, the release rate becomes slow as the amount of polyethylene oxide or the natural gum increases. Especially, the tablets of Examples 1 and 7 release the drug continuously in a release pattern similar to that of the comparative formulation.

Test Example 2

In Vitro Release-Test

In vitro release-tests were conducted for the tablets prepared in Example 1 and the comparative formulation by repeating the method of Test Example 1, except for changing the rotation rate to 75 rpm, 100 rpm and 150 rpm.

Figure 5:
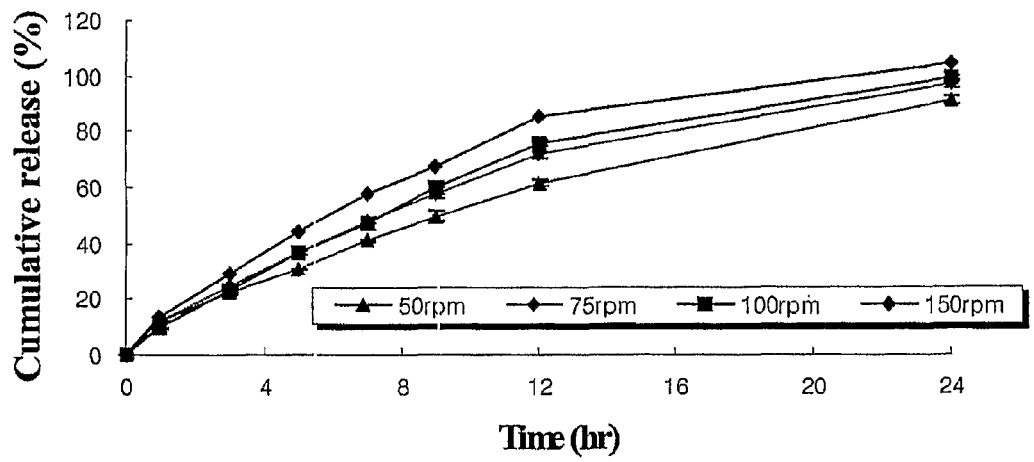
FIG. 5: the change in the in vitro release profile of the sustained release tablet prepared in Example 1 of the present invention as function of the rotation ratio of the release port.
Figure 6:
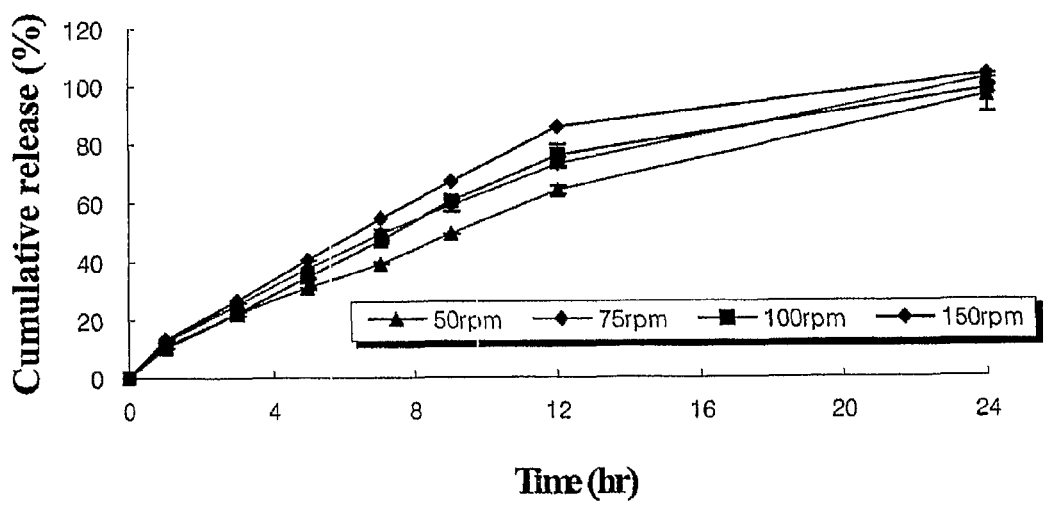
FIG. 6: the change in the in vitro release profile of a comparative formulation (NIASPAN®) as function of the rotation ratio of the release port.

As can be seen from FIGS. 5 and 6, the tablet of Example 1 displays a steady release pattern equal to that of the comparative formulation, without initial burst release of the drug even at a high rotation rate.

Test Example 3

In Vitro Release-Test

In vitro release-tests were conducted by repeating the method of Test Example 1, except for using the tablets prepared in Example 7, and Comparative Examples 1 to 3.

Figure 7:
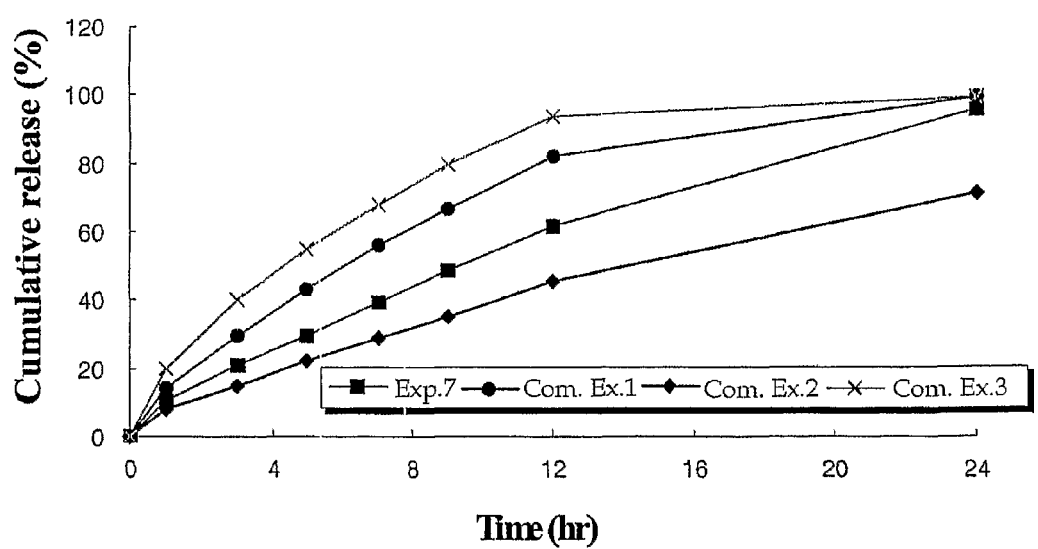
FIG. 7: in vitro release profiles of the sustained release tablets prepared in Example 7 and Comparative Examples 1 and 3.

As can be seen from FIG. 7, tablet of Comparative Examples 1 without polyethylene oxide and tablet of Comparative Examples 3 without natural gum show burst drug release at the initial stage, and tablet of Comparative Example 2 without the polyvinyl acetate/polyvinyl pyrrolidone mixture shows a release rate much slower than the desired release rate.

While the invention has been described with respect to the above specific embodiments, it should be recognized that various modifications and changes may be made and also fall within the scope of the invention as defined by the claims that follow.

What is claimed is:

1. A sustained release composition for oral administration of niacin, comprising niacin as an active ingredient; a carrier for sustained release composed of a hydrophilic polymer and a hydrophobic polymer; and a pharmaceutically acceptable additive, wherein the hydrophilic polymer is a mixture of a polyethylene oxide and a natural gum, the natural gum being a mixture of xanthan gum and locust bean gum; and the hydrophobic polymer is polyvinyl acetate or a mixture of polyvinyl acetate and polyvinylpyrrolidone.

2. The composition of claim 1, wherein niacin and the carrier are used in a weight ratio ranging from 1:0.01 to 1:1.

3. The composition of claim 1, wherein the hydrophilic polymer and the hydrophobic polymer are used in a weight ratio ranging from 1:0.1 to 1:2.0.

4. The composition of claim 1, wherein the weight ratio of polyethylene oxide : natural gum ranges from 1:0.01 to 1:5.0.

5. The composition of claim 1, wherein the polyethylene oxide has an average molecular weight ranging from 100,000 to 7,000,000.

* * * * *